US007204923B2

(12) United States Patent
Cummings

(10) Patent No.: US 7,204,923 B2
(45) Date of Patent: *Apr. 17, 2007

(54) CONTINUOUS FLOW DIELECTROPHORETIC PARTICLE CONCENTRATOR

(75) Inventor: Eric B. Cummings, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 370 days.

This patent is subject to a terminal disclaimer.

(21) Appl. No.: 10/176,322

(22) Filed: Jun. 20, 2002

(65) Prior Publication Data

US 2003/0010637 A1 Jan. 16, 2003

Related U.S. Application Data

(63) Continuation-in-part of application No. 09/886,165, filed on Jun. 20, 2001, now Pat. No. 7,014,747.

(51) Int. Cl.
*G01N 27/26* (2006.01)
*G01N 27/447* (2006.01)

(52) U.S. Cl. ...................... 204/547; 204/643; 204/450; 204/600

(58) Field of Classification Search ................ 204/450, 204/600, 547, 643
See application file for complete search history.

(56) References Cited

U.S. PATENT DOCUMENTS 3,162,592 A 12/1964 Pohl
4,326,934 A 4/1982 Pohl
4,737,251 A 4/1988 Carle et al.
4,830,726 A 5/1989 Stamato et al.
5,106,468 A 4/1992 Chimenti
5,178,737 A 1/1993 Lai
5,286,434 A 2/1994 Slater et al.
5,814,200 A 9/1998 Pethig et al.
5,837,115 A * 11/1998 Austin et al. ............... 204/450
5,888,370 A 3/1999 Becker et al.
6,071,394 A 6/2000 Cheng et al.
6,254,754 B1 * 7/2001 Ross et al. .................. 204/548
6,596,144 B1 7/2003 Regnier et al.
6,824,664 B1 * 11/2004 Austin et al. ............... 204/643

FOREIGN PATENT DOCUMENTS

WO WO 99/33559 7/1999
WO WO 01/37958 5/2001

OTHER PUBLICATIONS

Cummings, et al., "Dielectrophoretic Trapping Without Embedded Electrodes," Microfluidic Devices and Systems III, Proceedings of SPIE, Sep. 18-19, 2000, vol. 4177, pp. 164-173.

* cited by examiner

*Primary Examiner*—Nam Nguyen
*Assistant Examiner*—Jeffrey Barton
(74) *Attorney, Agent, or Firm*—McDonnell Boehnen Hulbert & Berghoff LLP

(57) ABSTRACT

A continuous-flow filter/concentrator for separating and/or concentrating particles in a fluid is disclosed. The filter is a three-port device an inlet port, an filter port and a concentrate port. The filter separates particles into two streams by the ratio of their dielectrophoretic mobility to their electrokinetic, advective, or diffusive mobility if the dominant transport mechanism is electrokinesis, advection, or diffusion, respectively.

Also disclosed is a device for separating and/or concentrating particles by dielectrophoretic trapping of the particles.

8 Claims, 18 Drawing Sheets

CONTINUOUS FLOW DIELECTROPHORETIC PARTICLE CONCENTRATOR

CROSS-REFERENCE TO RELATED APPLICATIONS

This is a continuation-in-part of U.S. patent application Ser. No. 09/886,165 filed Jun. 20, 2001, now U.S. Pat. No. 7,014,747 which is incorporated herein by reference.

STATEMENT OF GOVERNMENT INTEREST

This invention was made with Government support under contract no. DE-AC0494AL85000 awarded by the U.S. Department of Energy to Sandia Corporation. The Government has certain rights in the invention.

FIELD OF THE INVENTION

This invention is in the field of separating particles.

BACKGROUND OF THE INVENTION

Electrokinesis and dielectrophoresis are two technologically important particle and fluid transport mechanisms in microscale flow channels. In the former, particle or fluid transport is produced by an applied electric field acting on a fluid or particle immersed in a fluid having a net mobile charge and is widely used as a mechanism for manipulating particles and conveying fluids in Microsystems.

Dielectrophoresis is particle motion produced by an electric field gradient on the induced dipole moment of a particle and the surrounding fluid. Rather than being linear in the applied field as is the case with electrokinesis, the dielectrophoretic potential field experienced by a particle is second order in the local electric field and is proportional to the difference between the particle and fluid polarizabilities.

Dielectrophoresis finds extensive application in manipulating, fusing, sorting, and lysing biological materials. However, prior art dielectrophoretic applications have the disadvantage that they require not only the use of networks of embedded electrodes that can be difficult and costly to fabricate to accomplish the desired result but also application of an alternating electric field having zero mean value. Because prior art dielectrophoretic separations apparatus depends upon the use of an applied electric field to effect separation, fluid flow through such an apparatus must be pressure-driven. Electrokinetic or electric field-driven flow cannot be used because of interferences with the electric field produced by the embedded electrodes and its attendant effect upon the separations process. Pressure-driven flow produces more hydrodynamic dispersion of an analyte than electrokinetically driven flow. Moreover, the prior art employs electrodes that produce field gradients in three dimensions, e.g., electrodes deposited on the top, bottom, or both surfaces of a channel. The dielectrophoretic effect decreases away from these electrodes. This decrease limits the maximum depth of the channels over which dielectrophoresis is effective. Channels cannot be made arbitrarily deep to support a desired volumetric flow rate or sample throughput. The depth dependence of the dielectrophoretic effect is also a source of analyte dispersion in a separation.

Articles entitled Dielectric Trapping Without Embedded Electrodes by E. B. Cummings and A. K. Sing in AIAA Ideal Electrokinesis and Dielectrophoresis in Arrays of Insulating Posts by Eric B. Cummings, AIAA February, 2001 describe scientific principle related to particle behavior in arrays of insulating structures. PCT US00/41929, Nov. 6, 2000 having a priority of application No. 60/163,523 describes trapping of particles using electrode-less dielectrophoresis for polarizable particles. All of these references are incorporated herein by reference.

SUMMARY OF THE INVENTION

The invention encompasses devices having insulating structures within a flow channel for separating particles. These insulating structures provide dielectric potential barriers for particles such that fluid can flow past the barriers, but particles are redirected. The dielectric barriers result from non-uniform electric fields produced by the insulating structures. Placing these structures in an array enhances throughput, separation efficiency, and robustness against fouling of the device.

BRIEF DESCRIPTION OF THE FIGURES

FIG. 2(*b*) shows a gray-scale plot of the dielectrophoretic potential.

FIG. 2(*c*) shows a plan view of the three-port continuous-flow DEP filter/concentrator based on flow depicted in FIGS. 1(*a*) and 1(*b*).

FIG. 5(*b*) shows a multiple column continuous flow device.

FIG. 5(*c*) shows a device with the addition of a waste port.

DETAILED DESCRIPTION OF THE INVENTION

Figure 1:
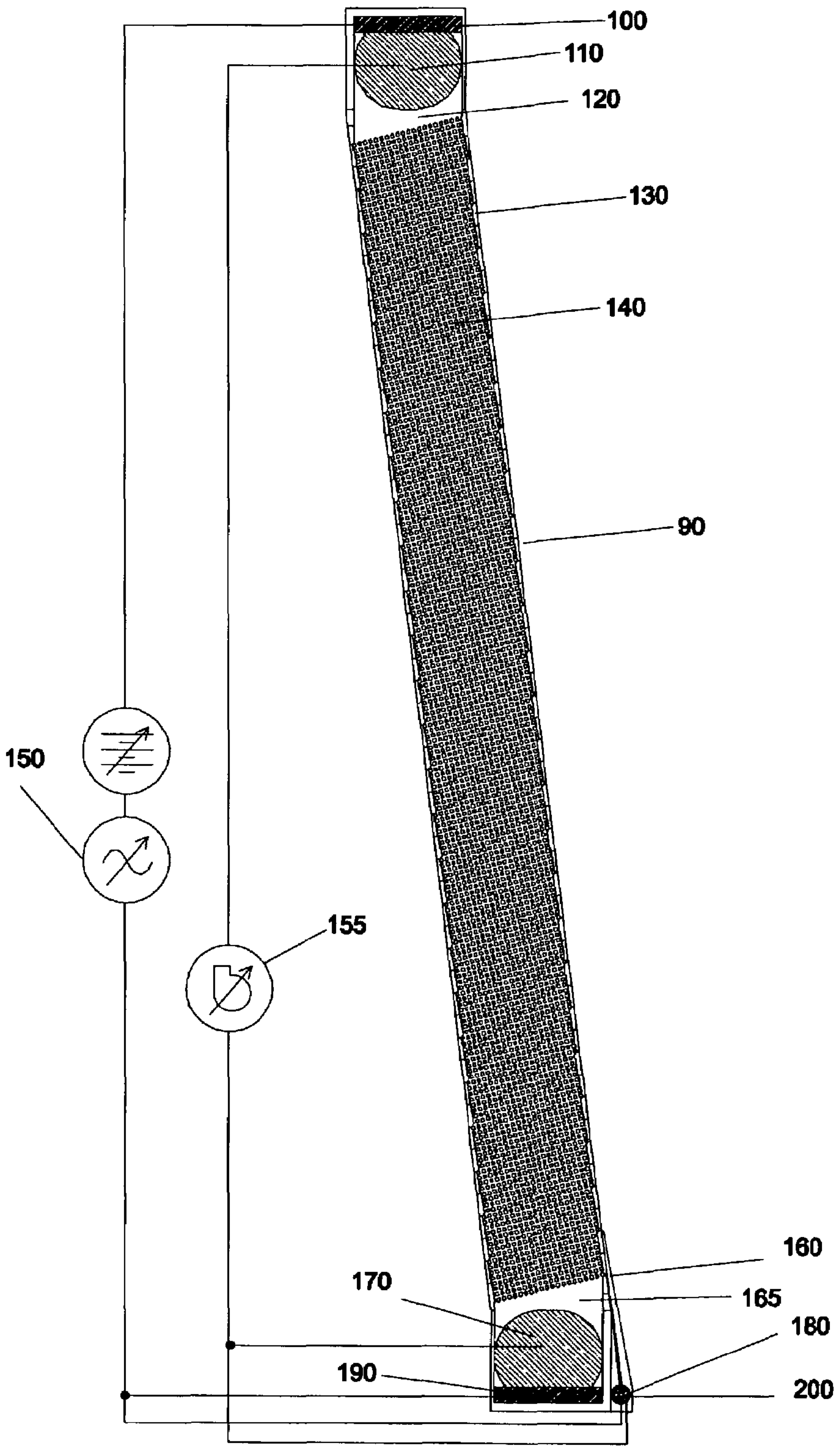
FIG. 1 is a schematic diagram of one example of a device for carrying out the present invention.

The invention encompasses devices based on filamentary dielectrophoresis having insulating structures within a flow channel. The insulating structures provide the non-uniform electric field required for the dielectrophoretic separations. The devices are useful for separating particles.

As used in this specification, the term "particle" refers generally to biological as well as non-biological matter that can be in the size range of from about 5 nm to 200 μm, such as proteins, DNA, RNA, assemblages of molecules, viruses, plasmids, bacteria, cells or assemblages of cells, protozoa, embryos, or other small organisms, minerals, crystals, colloids, and gas bubbles. The term "spatial separation" is used to describe a process by which particles within a fluid are filtered, concentrated, immobilized, retarded, or advanced relative to the bulk fluid or dissimilar particles. An axis of an array is a direction in which the fluid flow streamlines or electric field lines substantially repeat following an integral number of passages through cells of the array. Principal axes are those that minimize the number of cell passages between repeats of the streamlines. An "applied electric field" relates to the electric field produced by applying a voltage to electrodes in communication with the dielectrophoretic flow system.

In order to understand the invention better, the following brief discussion is provided.

Dielectrophoresis (DEP) is the motion of particles toward or away from regions of high electric field intensity. When an external electric field is applied to a system consisting of a particle suspended in a fluid medium, charges are induced to appear at the particle-fluid interface so as to confer on this polarized particle the properties of an electric dipole. The electrostatic potential of a polarizable particle is minimized in regions of highest electric field intensity. If the particles are immersed in a polarizable fluid, the electrostatic energy of the system is minimized by placing the most polarizable component in the high-field regions. If the particle is more polarizable than the fluid, it will be impelled toward a region of high field intensity (positive dielectrophoresis) or otherwise toward a region of lower field intensity (negative dielectrophoresis). The polarization of particles occurs by a variety of mechanisms having characteristic relaxation times. The frequency variation of the net polarization is a means of obtaining information about or manipulating particles on the basis of their internal and external physical structure. In DEP, the force on a particle and its surrounding medium is proportional to the gradient of the field intensity and is independent of the direction of the electric field. This is in contrast to electrophoresis, the field induced motion of charged particles, wherein the direction of the force on a particle is dependent upon the sign of the charge and the direction of the field.

For a particle to experience either positive or negative DEP it must be subject to a spatially non-uniform electric field. Conventionally, these inhomogeneous fields are produced by the use of various electrode geometries, such as disclosed in U.S. Pat. Nos. 3,162,592 and 5,814,200. However, as will be shown below spatially inhomogeneous fields can be created by the use of insulating structures disposed in flow channels.

Because the dielectrophoretic effect is of second order in the applied electric field, it is negligible at suitably low applied fields. In this limit, the dominant particle-transport mechanisms are electrokinesis and diffusion. Advection and electrokinesis do not induce changes in particle concentration for a uniform fluid having a dilute, initially uniform particle concentration. Diffusion, hydrodynamic dispersion, and electrostatic repulsion overwhelm weak dielectrophoresis so no appreciable spontaneous particle concentration gradients form. However, the behavior of particles in mixed DEP and advective/electrokinetic flows changes qualitatively near two threshold applied electric fields: a threshold in which DEP begins to dominate diffusion and a threshold in which DEP becomes comparable to and greater than advection and electrokinesis.

Assuming, as is typically the case, the Peclet number of the particles in the flow is greater than unity, the former threshold occurs at a lower applied electric field than the latter. Above this lower threshold, "filaments" having enhanced or depleted particle concentration appear primarily along flow streamlines. These filaments form when dielectrophoresis begins to produce concentration gradients in the flow. Filamentary dielectrosphoresis is the physical basis for one aspect of the invention which provides a continuous flow filter/concentrator.

The second threshold in mixed dielectrophoretic and electrokinetic flows occurs at an applied electric field in which the local DEP force exceeds the electrokinetic and hydrodynamic drag force. Above this threshold, regions appear where particles are "trapped" by the DEP field. The number of particles in the trap grows in time until the applied field stops, the particles fill the region of the trap, or the presence of particles modifies the trap by perturbing the electric field and electroosmotic flow. Trapping dielectrophoresis is the physical basis of a second aspect of the invention.

In one aspect, the invention relates to a continuous flow filter/concentrator of which filamentary dielectrophoresis is the physical basis. This filter is a three-port device comprising of one inlet and two outlet ports: a "filter" port and a "concentrate" port. The filter separates particles into two streams by the ratio of their dielectrophoretic mobility to their electrokinetic, advective, or diffusive mobility if the dominant transport mechanism is electrokinesis, advection, or diffusion, respectively. The filter has a low-pass characteristic in that particles having a mobility ratio below a threshold value pass relatively unimpeded to the filter port, while the other particles are concentrated and transported to the concentrate port. The device works by forming a dielectrophoretic (DEP) potential barrier that is overcome by the dominant transport mechanism only if the mobility ratio is below a threshold value.

One embodiment of a device of the invention is shown in FIG. 1. The device comprises a fluid flow channel 90, input electrode 100, an input port 110, an array of insulating structures 140, a voltage waveform source 150, electrodes 180 and 190, a filtered output port 170 and a particle concentrate port 200.

The fluid flow channel 90 is located in a device substrate. The substrate can be made of a variety of materials including glass and plastic. If the substrate is glass the fluid channel can be isotropically etched into the glass. The flow channel is optionally enclosed, for example, with a thermally bonded glass cover.

The input electrode 100 may be deposited on the device substrate, or it may be free-standing, or be located externally in an input reservoir or upstream of previous devices, provided it is in electrical communication with an input channel 120 so that electric field lines in the input channel are aligned with the side walls of the input channel.

Input port 110 may be drilled, cut, or punched in either the top or bottom substrate material or may be simply a continuation of the input channel 120 upstream to another device. The side walls 130 of the device are a barrier to fluid motion and may be solid, liquid, gaseous, or virtual (aligned with a fluid streamline) provided there is no substantial transport of the flowing liquid across them.

The insulating structures 140 comprise a plurality of posts or columns of various possible sizes and shapes and can be arranged in various non-repetitive patterns and packing configurations. Like the side walls, the posts 140 can be solid, liquid, gaseous, or virtual provided they produce dielectrophoretic potential barriers along the columns of the array. The insulating structures can be formed during the flow channel etching process. The packing or array of insulating structures is tilted slightly with respect to the applied electric field by between 0.5 and 15°, preferably 5–10°. The posts are preferably between about 10 to 1000 times larger than the particles being concentrated or separated. For example, the posts in an array for separating bacteria of about 1 μm are preferably about 50–200 μm in diameter. For viruses, the posts are preferably about 1–20 μm in diameter.

Voltage waveform source 150 drives electrophoresis and possibly electrokinesis. The total applied voltage RMS is preferably about 1–200 V/mm (combination of AC and DC voltage). The device can contain an optional source of pressure driven flow 155. The device shown also includes a channel 160 at the base of the array that channels the concentrated particles to a spatially distinct stream. As shown, the stream is separated from the filtered channel 165 by a solid boundary. Again, this boundary can be solid, liquid, gaseous, or virtual provided the streams remain substantially distinct. The filtered output port 170, like the input port 110, may be a passage through the top and/or bottom substrate material or may be continued downstream by another device. The electrodes 180 and 190 are in electrical communication with the concentrate and filtered channels and, like the input electrode 100, may be deposited, free-standing, external, or downstream of subsequent devices. Electrodes 180 and 190 may be distinct or connected. If they are distinct, they may be connected to the same or different voltage waveforms. Finally, the particle concentrate output port 200, like the input port 110 and filtered output port 170, may pass concentrate out of the substrate or further down the substrate to subsequent devices.

Figure 2:
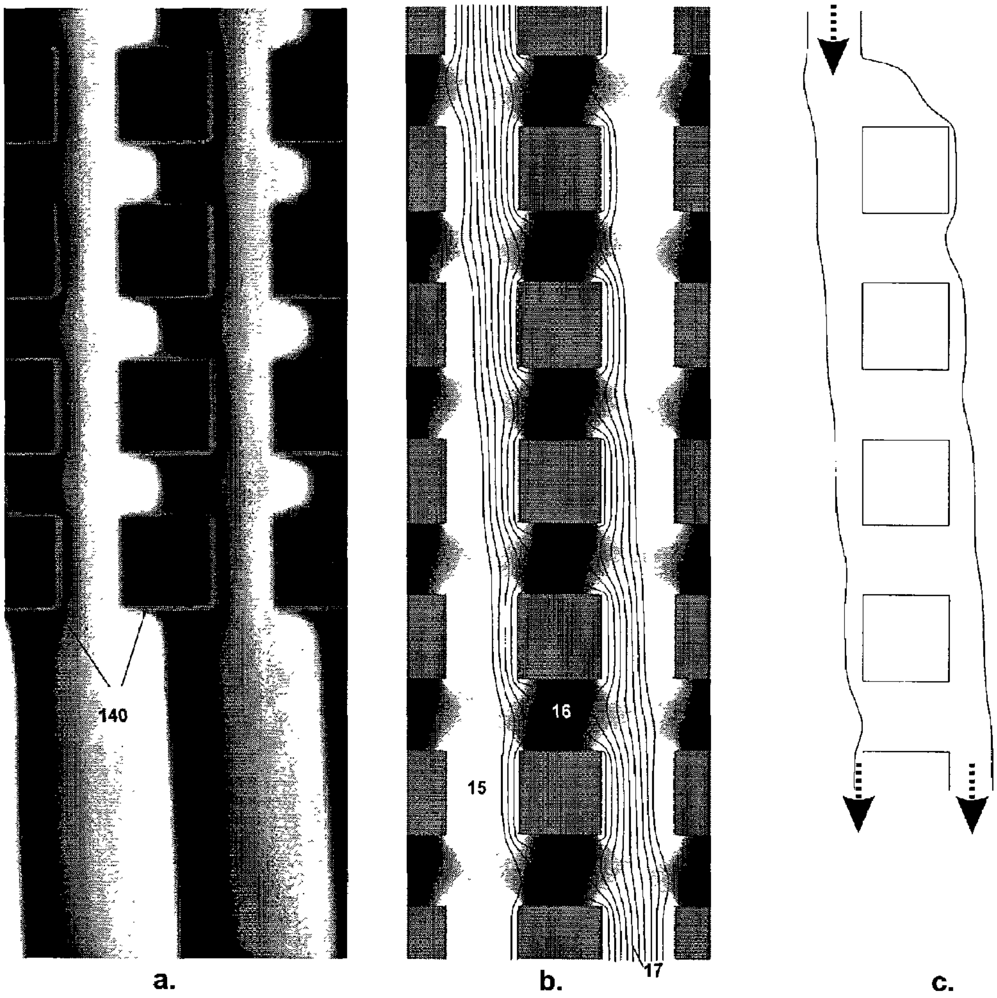
FIG. 2(*a*) shows an experimental observation of a concentration and filtration effect of DEP in an array of square posts.

The DEP potential barrier in the devices of the invention is formed by creating regions of the fluid having a relatively weak electric field through which the unfiltered fluid passes relatively slowly. Such near-stagnant regions are formed between posts in the array of posts (140 in FIG. 1). FIG. 2*a* shows an experimental observation of this concentration and filtration effect; shown is a particle fluorescence image depicting filamentary filtration in an array of square posts 140. FIG. 2*b* shows a gray-scale image of the dielectrophoretic potential within the array ranging from white (low) 15 to black (high) 16. Electrokinetic flow streamlines 17 are superimposed to show how the fluid gradually is forced through the DEP potential barriers between the posts. The DEP barriers between the posts reject the particles, producing the observed filtration/concentration effect. FIG. 2*c* shows a plan view of a three-port device that operates on this principle. The wall contours of this device follow electrokinetic flow streamlines from FIG. 2*b*, thus the electric and electrokinetic fields within the device are the same as those found in FIG. 2*b*.

Figure 3:
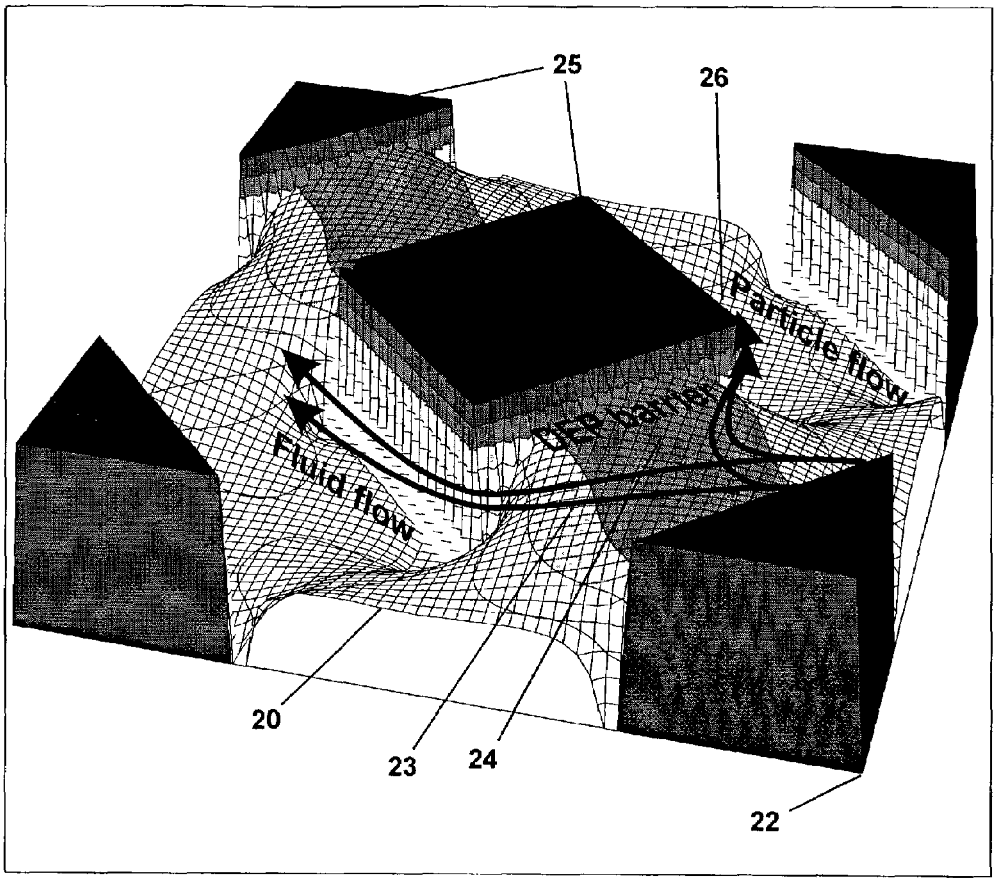
FIG. 3 shows a plot of the dielectrophoretic potential experienced by polarizable particles flowing through a cell of the array in FIG. 1(*b*).

FIG. 3 shows a plot of the dielectrophoretic potential surface 20 experienced by polarizable particles flowing through a cell of the array shown in FIG. 2*b*. The applied field is from the lower right corner 22 to the upper left corner with a slight bias toward the left (7.5°). This bias produces a small fluid flux 23 over the DEP barrier 24 between the rows of posts 25. As shown schematically in FIG. 3, particles having a DEP mobility ratio above the threshold value do not overcome the potential barrier and instead are concentrated along the right edge of the post 26. Particles having a DEP mobility ratio that is comparable but lower than the threshold value are also affected by the barriers and can be substantially removed from the cross-barrier flow by employing redundant columns of posts.

The shape and arrangement of posts in an array of posts can be optimized to enhance a particular behavior, something that is not possible in a randomly packed medium. The boundary edges of the insulating structures, in horizontal cross-section, can all be derived from components of simple shape primitives such as straight lines, cusps, concave and/or convex curves, and acute angles of which square and circular posts are examples. Moreover, these simple shape primitives can be used either singly or in combination to enhance the desired transport. The insulating structures in a particular arrangement can also be of more than one size.

The insulating structures or posts can be joined or overlapping in such a way as to make a solid wall through which particles cannot pass. Such posts can be etched so that the cross-sectional plane is oriented into the substrate. The posts need not be two-dimensional or intersect with either top or bottom bounding surfaces of the fluid. For example, the posts can be hemispherical bumps on a substrate surface, substantially cylindrical structures that stop short of the top surface and thereby create a field concentration above them, or posts that extend through the liquid-gas interface in a flow channel.

The shape and spacing of the posts and their orientation with respect to the applied electric field determine the magnitude and shape of the DEP potential barrier. The fluid flux across the DEP potential barrier is proportional to the angle the array makes with the applied electric field or mean advective flow. Smaller angles provide for a lower mobility ratio threshold or lower operating voltage at a given mobility ratio. Preferred angles are in the range of 0.5° through 15°. Above approximately 10°, the posts are designed to ensure a sufficient potential barrier exists between the posts. Preferred post shapes have the following characteristics:

1. Large radii of curvature to prevent local field concentrations and undesirable trapping of particles.

2. A straight or concave curve in the region between the posts to lower the electric field and prevent field concentration in the DEP potential barrier region.

Figure 4:
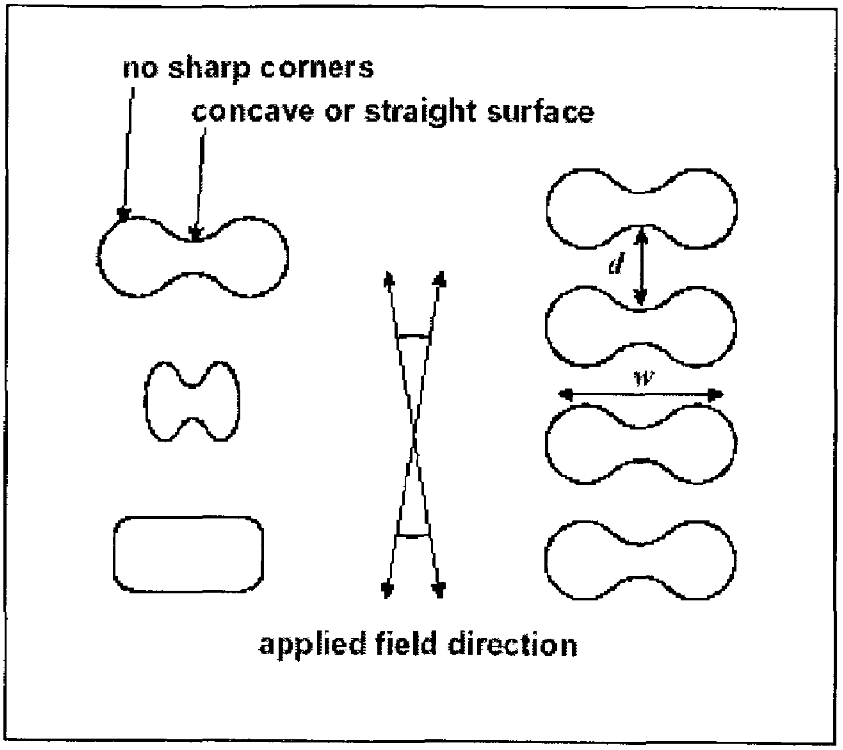
FIG. 4 shows examples of preferred dielectric structure shapes.

FIG. 4 shows examples of such posts. The distance (d) between rows of posts should be sufficiently small compared to the post width (w) that a well-defined and uniform potential barrier is formed between them. The spacing between columns of posts is less critical provided it is larger than approximately the radius of curvature of the posts so the posts do not excessively concentrate the field and produce undesired DEP traps.

Figure 5:
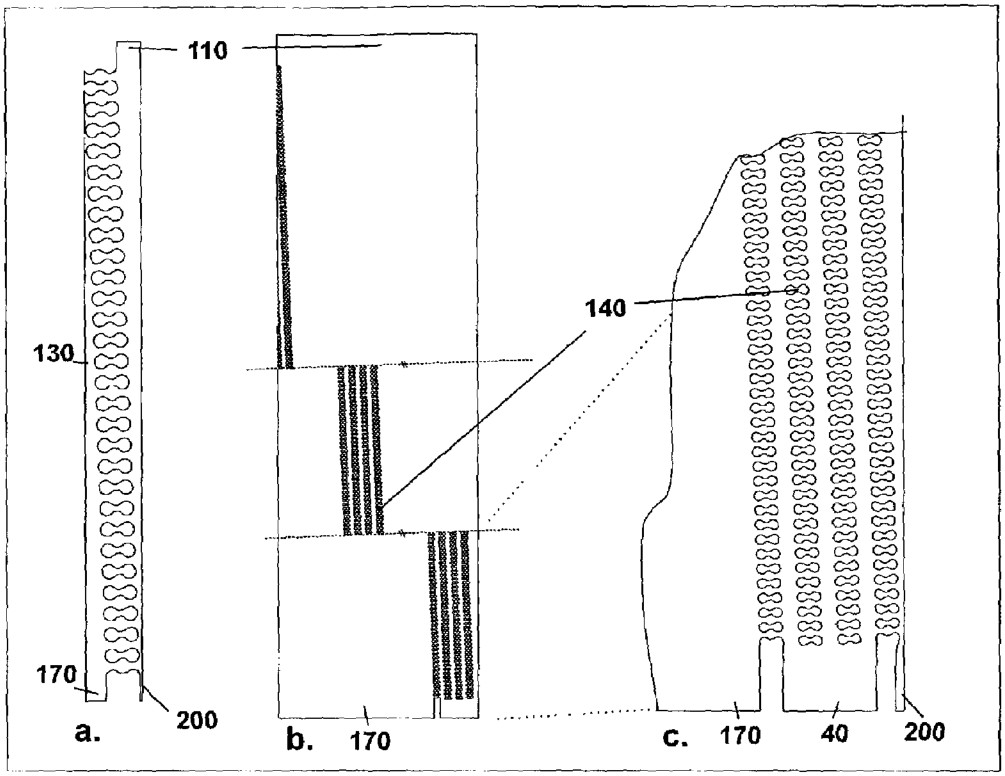
FIG. 5(*a*) shows a single column continuous flow DEP device.

FIG. 5 shows three examples of preferred embodiments of the device of the invention. The inlet port 110 is at the top, the filter port 170 is at the bottom left and the concentrate port 200 is at the bottom right of the devices. Electric fields are applied remotely (not shown in the drawing). The devices work on the same principle, but the device in FIG. 5*b* facilitates greater fluid throughput. The multiple columns of posts 140 provide redundancy if exceptionally good filtration is required. The number of columns can be increased arbitrarily to improve filtration or decreased to a single column. However, the degree of concentration of the concentrate stream is reduced when multiple columns of posts are employed. FIG. 5*c* shows a solution to the problem when both a high degree of filtration and high concentration factor are desired. A "waste" port 40 is added between the filter and concentrate ports. The flow from this port contains the relatively small concentration of leakage particles. The choice of post shape was made for illustration purposes and is not intended to be limiting. Generally, a device in which the post design shown is replaced by another that satisfies one or more of the characteristics listed above will function according to essentially the same principle, with differences in efficiency, threshold mobility ratio, or susceptibility to clogging, etc.

Figure 6:
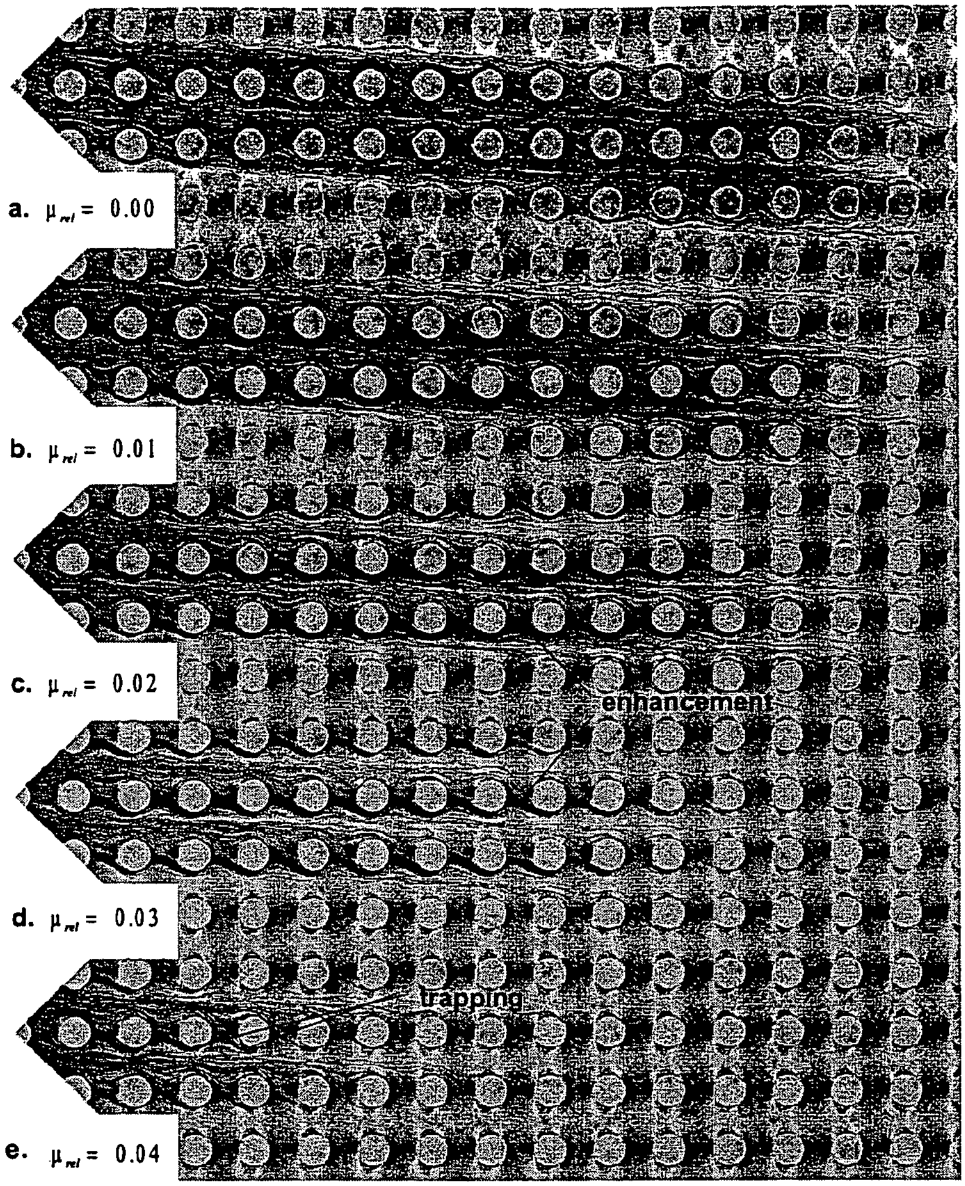
FIG. 6 is a simulation of enhancement-mode operation of a circular-post-array-based filter/concentrator.
Figure 7:
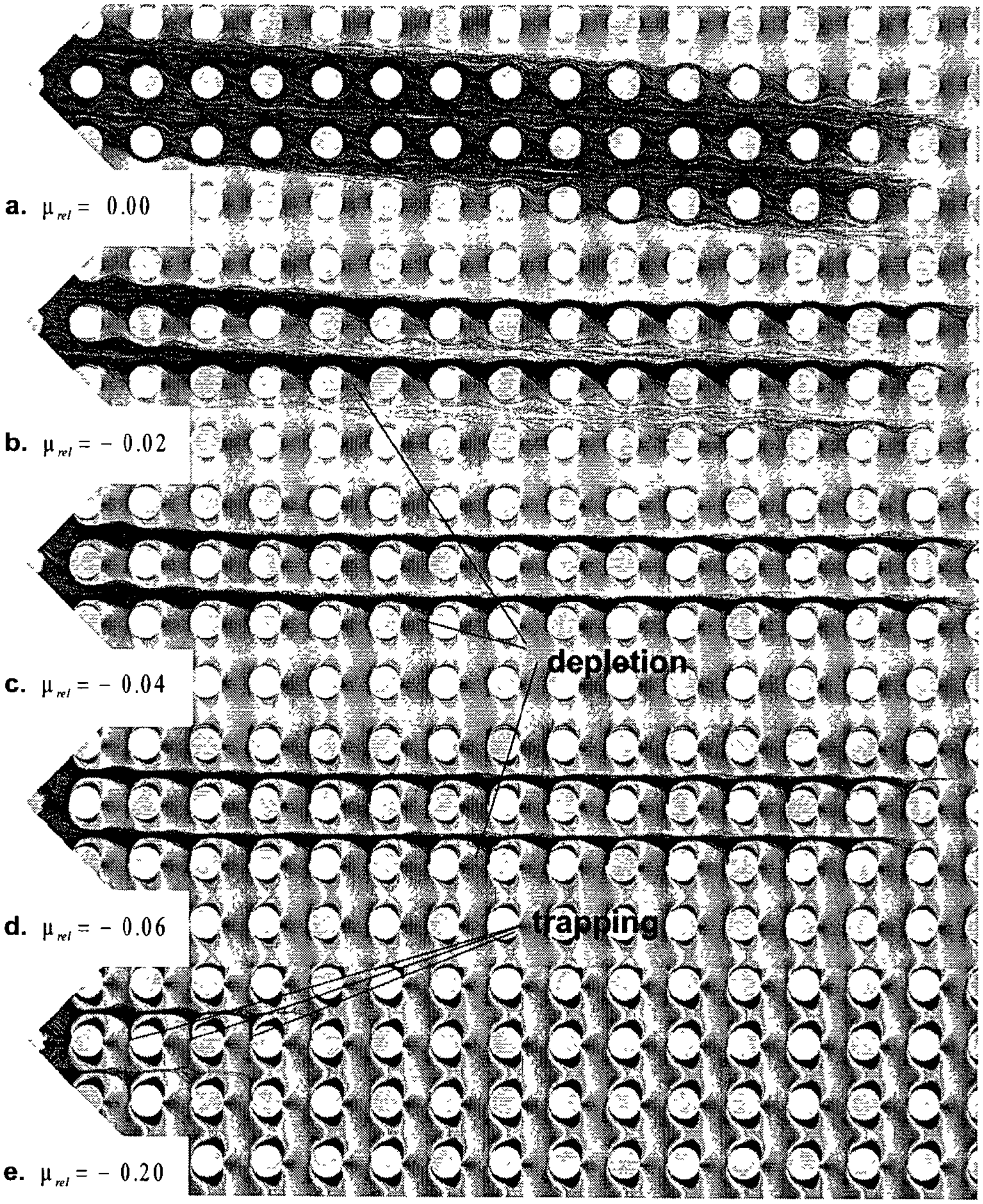
FIG. 7 is a simulation of depletion-mode operation of a circular-post-array-based filter/concentrator.

Filamentary dielectrophoretic concentrators can be designed to operate both in a "depletion mode," in which particles are rarefied by potential barriers along the columns of posts and an "enhancement mode," in which particles are concentrated by potential valleys along columns of posts. FIG. 2*a* shows depletion mode concentration and filtration of particles having positive dielectrophoretic mobility. The same array will operate in an enhancement mode for particles having negative dielectrophoretic mobility, with particles concentrated on the opposite side of the columns from the depletion-mode operation. FIG. 6 shows a simulation enhancement-mode operation for particles having positive dielectrophoretic mobility. Particles having a dielectrophoretic mobility above the filter threshold (approximately 0.01 arbitrary units) follow columns because of their enhancement effect. Particles having a dielectrophoretic mobility above the trapping threshold (approximately 0.035) become trapped on the post surfaces. The gray-scale background does not indicate concentration. FIG. 7 shows a depletion-mode operation for particles having negative dielectrophoretic mobility within a filter/concentrator based on a tilted circular-post-array. The variation in particle behavior with mobility is similar to that for enhancement-mode operation, but the thresholds, shapes and locations of filaments are different. The gray-scale background does not indicate concentration. Particles whose dielectrophoretic mobility magnitude is lower than the device threshold, between the device threshold and higher trapping threshold, and greater than the trapping threshold respectively are free to flow across columns, can flow only along columns, and are trapped on posts within the array.

Engineering considerations used to design a depletion-mode and enhancement-mode filamentary dielectrophoretic filter/concentrator are similar, but differ in detail, for example, the shape of the post and the side of the columns of posts that the particles concentrate. Both types of devices contain the same functional design elements, but the geometric details of these elements depend on the mode of operation. Where there is a difference in geometry, the design that follows is specialized for a depletion-mode filamentary dielectrophoretic concentrator of particles having a positive dielectrophoretic mobility. Geometrical modifications for enhancement-mode operation and/or concentrating particles having a negative dielectrophoretic mobility can be made from the following discussion by a designer skilled in the art.

The sharpness in threshold DEP mobility of a filamentary DEP concentrator is maximized when all the DEP potential barriers in the filter have the same shape and height. This condition is achieved in the interior of a uniform infinite array of uniform posts. The interior of an optimal DEP filter is designed to appear to the flow as if the array of posts repeats infinitely in the plane of the device by:

1) contouring the side walls of the device to streamlines of the flow in the corresponding uniform infinite array of posts at the desired flow-tilt angle with respect to the applied field;
2) tilting the array-filled flow channel with respect to the open entry and exit ports to ensure the electric field is applied evenly across the tilted array;
3) patterning the walls at the entry and exit ports of the device to match free streamlines emerging from a semi-infinite array at the channel-tilt angle specified in 2); and/or
4) modifying the shape of the posts at the entry and exit rows of the array to prevent excessive field concentrations at the interfaces between the open- and patterned-channel sections.

Figure 8:
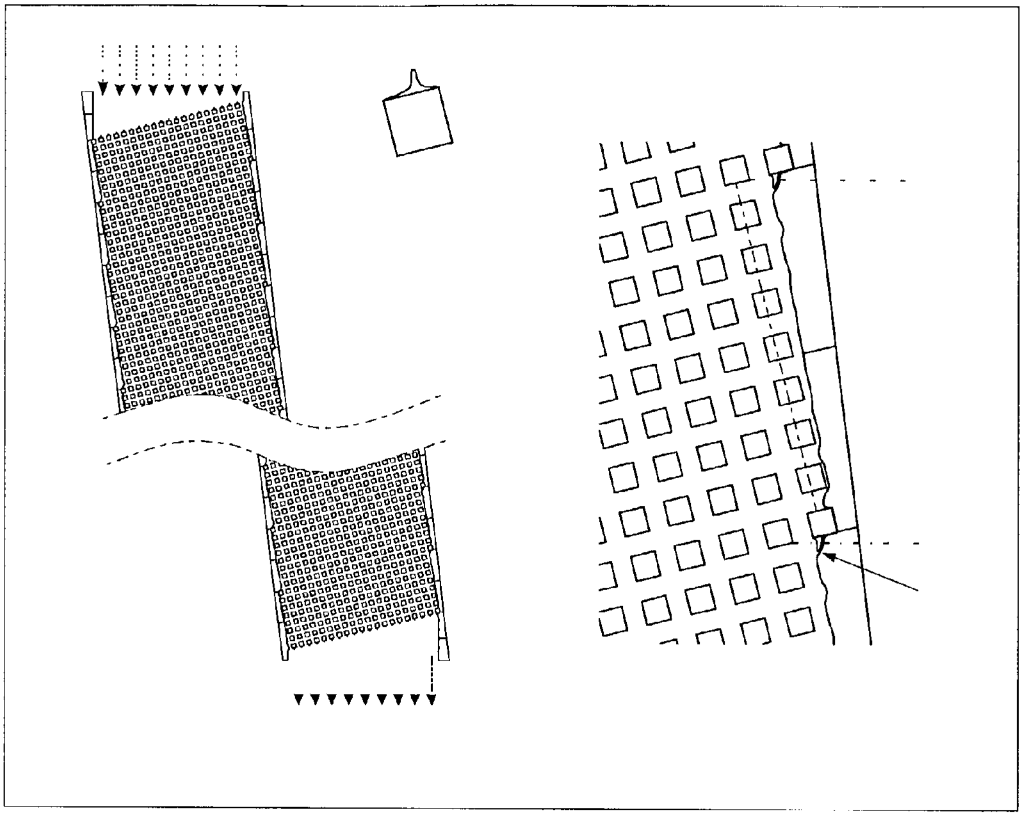
FIG. 8 shows a device having a uniform infinite array of posts.

These design details are illustrated in FIG. 8.

The inset at right shows a detail of the wall contouring. The flow-tilt angle has been adjusted so that the streamline patterns repeat after the passage of an integer multiple n of rows of posts. In the example shown, n=8. Generally, n is sufficiently large (e.g., greater than 8, preferably greater than 20) to produce the requisite DEP potential barriers between the posts. The parameter n need not be integral for the device to operate, but the details of the wall contouring become more complicated than in this example. The side walls for the full array (at left) are constructed by stacking copies of this 8-row pattern. By symmetry, the left wall is the same as the right wall rotated by 180 degrees.

Figure 9:
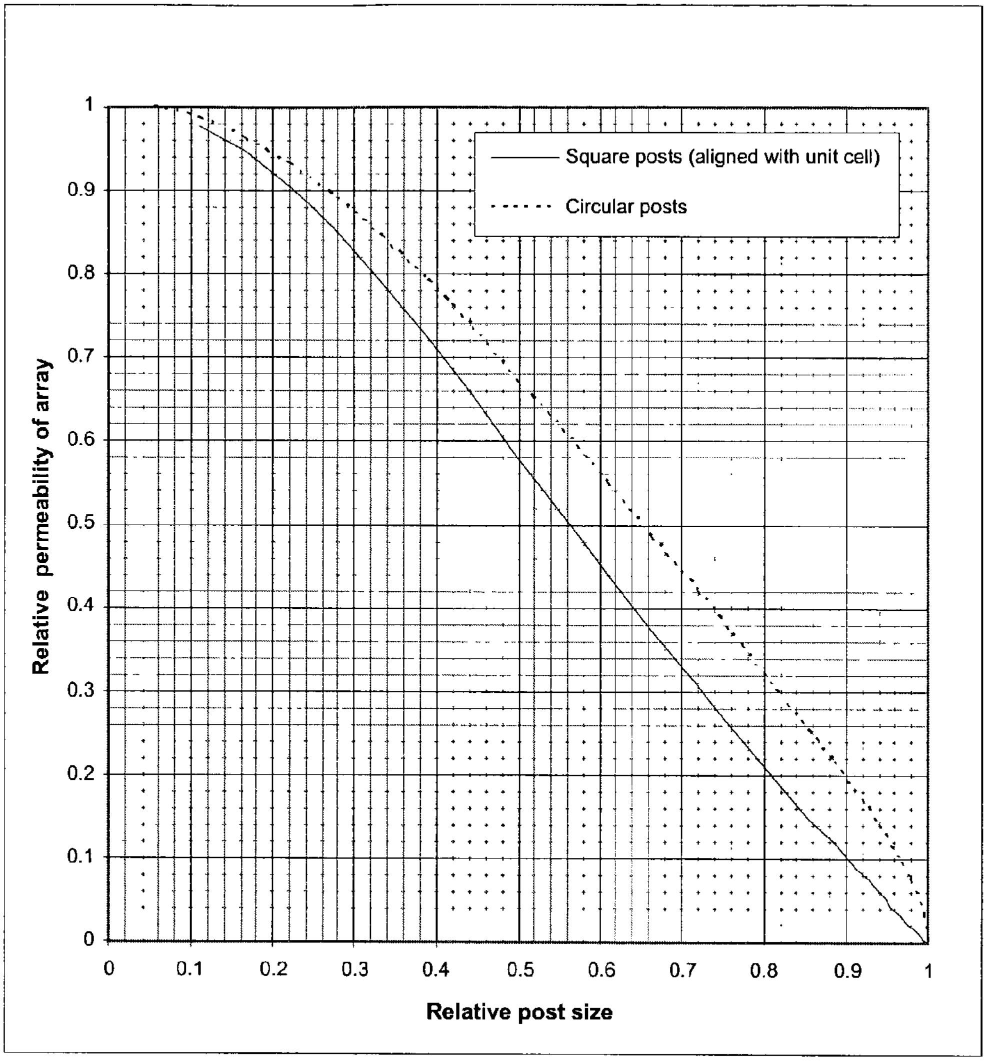
FIG. 9 Plot of array conductivity relative to an open channel versus post size scaled by the unit cell size.

The array-filled flow channel is tilted with respect to the entry and exit ports to obtain a uniform electric field across the array. The transition from open channel to tilted array appears to the electrical flow as an abrupt permeability change across a tilted straight interface. For the electric field to be constant along this interface, the flow-incidence angle of the interface should satisfy the compatibility relation $$\tan(\theta_i)/\sigma_i=\tan(\theta_a)/\sigma_a,$$

where θ is the angle of the flow with respect to the normal to the interface, σ is the effective permeability, and the subscripts 'i' and 'a' respectively refer to the incident and array flows. The effective permeability of the array is the ratio of the total current through the array to the applied electric field and is a function of post shape and size. For a post having symmetry of rotation through 90 degrees, the effective permeability does not depend on the flow angle through the array. FIG. 9 shows a plot of the effective permeability relative to that of an open channel ($\sigma_i/\sigma_a$) of square arrays of circular and square posts (edges aligned with rows and columns) versus post size. For general post shapes, the relative effective permeability is fixed by the choice of post and flow angle with respect to the columns of posts in the array ($\theta_a$, where $\tan(\theta_a)=1/n$). Thus the choice of post and flow angle (or n) uniquely determines the incidence angle, $\theta_i$, which appears in FIG. 8 as a tilt of the straight outer boundary of the channel side walls, or equivalently as a horizontal offset between the entry and exit ports.

Finally, the electric field at the entry and exit rows of posts is somewhat higher than that experienced in the interior of the array. To prevent particles from being trapped on these rows, the shape of the post should be modified slightly to reduce the field concentration. The "tippet" added to the top of the post, shown in the detailed inset in FIG. 8, is an example of a shape modification that locally reduces this field concentration while having a negligible impact on the flow in the neighboring rows.

All particles whose DEP mobility is between the threshold of the filter and the trapping threshold of the posts that are present in the liquid between the dashed line and the wall pass through the orifice indicated by the arrow (FIG. 8). Immediately above the arrow is a pan-handle-shaped post modifier that reduces the DEP barrier at that post, allowing particles to spill through the orifice to the next set of rows. Some alteration of either the post shape, wall contour, or a combination is needed in this region to weaken the DEP barrier. This region is analogous to a spillway of a dam.

The filter concentration factor can be calculated geometrically by considering only the column of posts next to the wall. If the array is tilted so streamline patterns repeat every n rows, the fluid flux passing between each row is a fraction 1/n of the total flux through the column. All particles whose DEP mobility is between the filter and trapping thresholds cross the columns through a single row at the wall. Thus the concentration factor per column is n. If there are m columns, and at least m sets of n rows in the array, the concentration factor is m n. For the array shown in FIG. 8 this factor is 160 (8 times 20). Having more than m sets of n rows in the array does not increase the concentration factor, but provides redundancy which improves robustness against clogging and other imperfections.

The device depicted in FIG. 8 does not show any explicit channeling to harvest the particles as they flow from the filter in a tight concentrated filament at the bottom right of the array. These geometries, e.g., inserting a splitter wall or side channel for the particles, are straightforward to incorporate into the design by someone skilled in the art. Alternatively one may extract particles by means of separate channels at the end of each grouping of n rows rather than permitting the particles to spill into the next set of rows. While this modification reduces the concentration factors, other design considerations may make this option attractive. Particle harvesting channels are considered to be external to the filter/concentrator, since they primarily perform particle extraction rather than filtration and concentration.

The design methodology that has been outlined applies to uniform rectilinear arrays of substantially uniform posts of any cross-sectional shape, not just square posts or square arrays. The performance of devices having alternative shapes will differ in efficiency, required electric field, clogging tolerance, etc., but not in the principles of operation or design.

The systems disclosed herein are noteworthy for their simplicity of fabrication. No diffraction-limited lithography, embedded electrodes or small/high-aspect-ratio structures are required to produce significant effects on particles in the range of 200-nm diameter. Consequently, these systems can be produced by methods well known in the art such as, but not limited to, casting, photopolymerization, isotropic and anisotropic glass or alumina etching, polymer etching, LIGA, and other mass-fabrication techniques. While the invention was illustrated by the use of glass substrates, polymer materials such as polymethylmethacrylate, polycarbonate, fluorocarbons, polyolefins, and epoxies can be used as substrate material.

Figure 10:
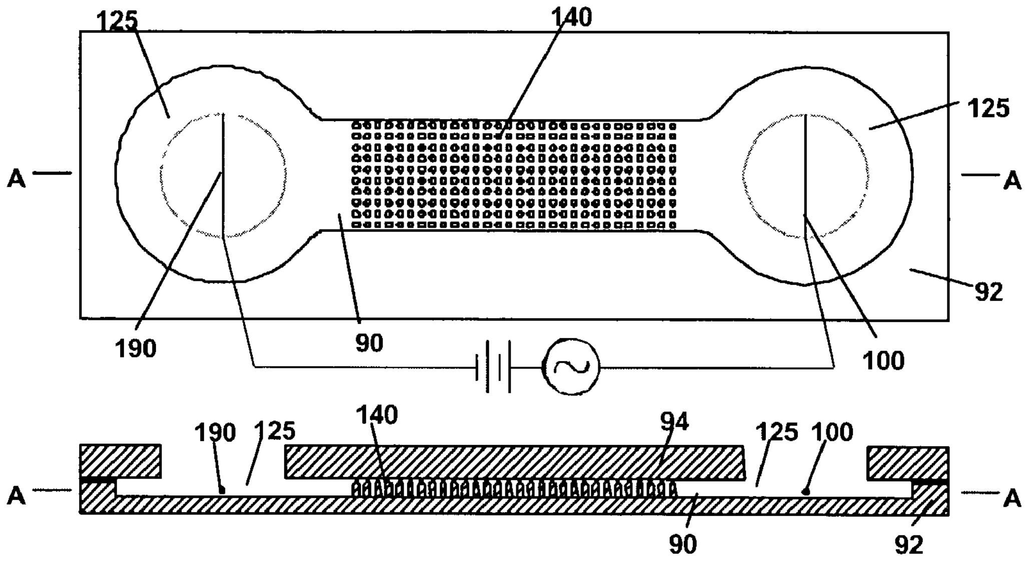
FIG. 10 is a schematic diagram of another example of a device for carrying out the present invention.

In another aspect, the invention provides a particle concentrator device of which trapping dielectrophoresis is the physical basis. A preferred device for carrying out this aspect of the invention is illustrated in FIG. 10. As will be understood by a person of skill in the art, the device illustrated in the FIG. 10 can also be used for filamentary dielectrophoresis, which is discussed in detail above. Further, the discussion about post sizes, shapes, manufacturing and optimization, etc., with respect to the device depicted in FIG. 1, is also applicable to the device depicted in FIG. 10.

The device shown in FIG. 10 comprises at least one fluid flow channel or conduit 90 isotropically etched into a glass substrate 92 with a thermally bonded glass cover 94 to enclose the flow channel. In this embodiment, flow channel 90 is approximately 7–9 μm deep and has a patterned arrangement or array of insulating structures 140 disposed therein. The insulating structures, formed during the flow channel etching process comprised a plurality of posts or columns of various sizes and shapes that can be arranged in various repetitive or non-repetitive patterns and packing configurations.

Reservoirs 125 are provided at the inlet and outlet ends of each channel. Each reservoir is in fluid communication with a flow channel and each has an electrode 100 and 190 in electrical communication therewith. The electrodes are attached to power supply means, such as a high voltage power supply capable of supplying either DC or AC power, to provide an electric field in each channel. The outlet reservoirs can be used to extract separated particles and the inlet reservoirs can be used to introduce a fluid suspension of particles to be separated into the patterned channels.

EXAMPLES

Figure 16:
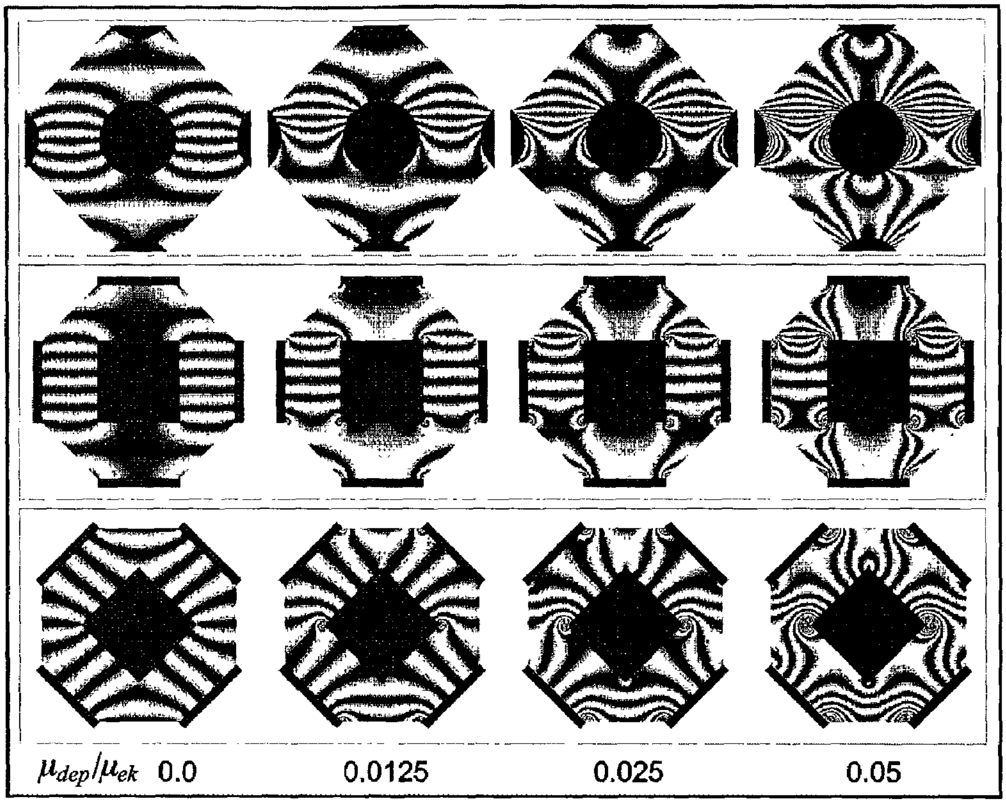
FIG. 16 is a graphical representation of the combined electrokinetic and dielectrophoretic potential, y, from within a cell comprising three kinds of uniform arrays.
Figure 17:
FIG. 17 shows the flow in the interior of a uniform square array of circular posts at an applied electric field of approximately 100 V/m.

In order to illustrate the effect of the insulating structures on electric field lines, a suspension of 200 nm diameter fluorescent latex microspheres in an aqueous 1 mM phosphate buffered saline solution maintained at pH 7.7 was supplied to the channel structures through the inlet reservoirs. Examples of filamentary DEP are illustrated in FIGS. 11–15 below. FIGS. 16–17 relate to trapping dielectrophoresis. These examples are for illustration purposes and are not intended to limit the scope of the invention.

Figure 11:
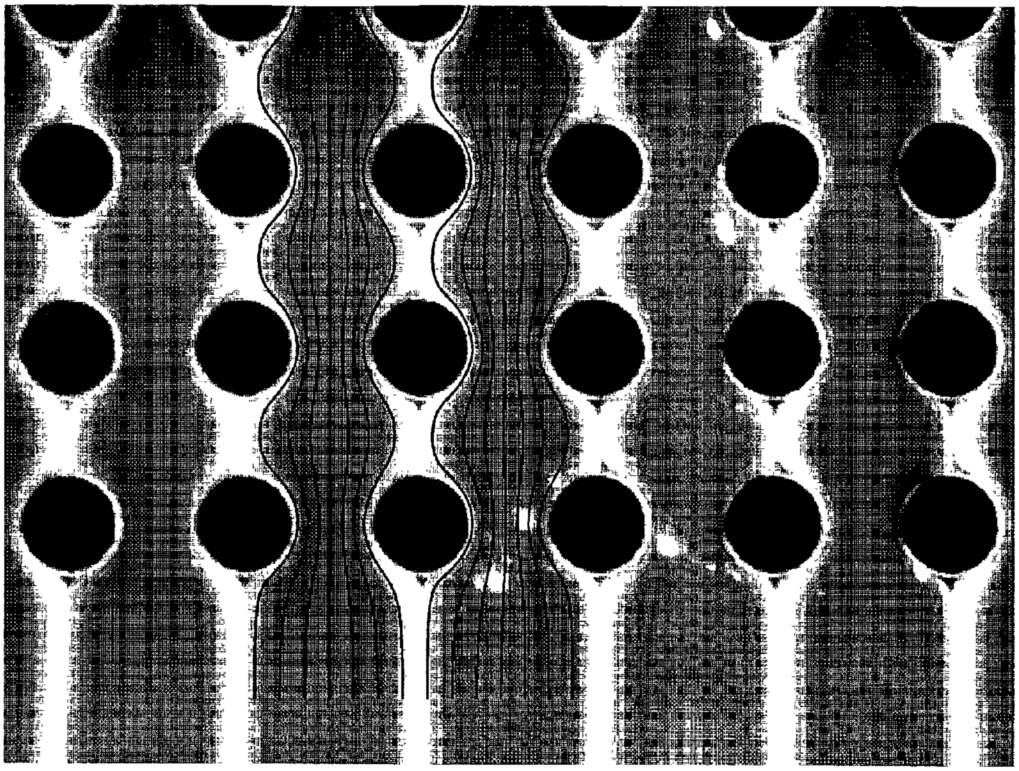
FIG. 11 shows the particle concentration variation in flow past a uniform square array of circular posts 56 posts long and 16 posts wide.

FIG. 11 shows the particle concentration variation in flow past a uniform square array of circular posts 56 posts long and 16 posts wide. The 33 μm diameter posts are arranged on 63 μm centers. In this example the electric field of 25 V/mm is oriented in alignment with an array of posts, a principal axis of the array. For purposes of illustrating their relationship to the particle filaments, electrokinetic flow streamlines are superimposed on the image. The gray scale of the image shows the relative intensity of particle fluorescence and is thus a measure of particle concentration. The thin bright border around each post is strong specular reflection of the illumination light and is not a fluorescence signal. In the figures below all flows are from the top of the figure to the bottom and produced by a voltage applied to remote electrodes.

It can be seen in FIG. 11 that the particle concentration varies little in the core flow between the post columns. Approaching the columns, the particle concentration increases several-fold. Near the stagnation streamline down the center of the column, the concentration dips significantly. This pattern of particle persists as the streamlines leave the post array.

Figure 12:
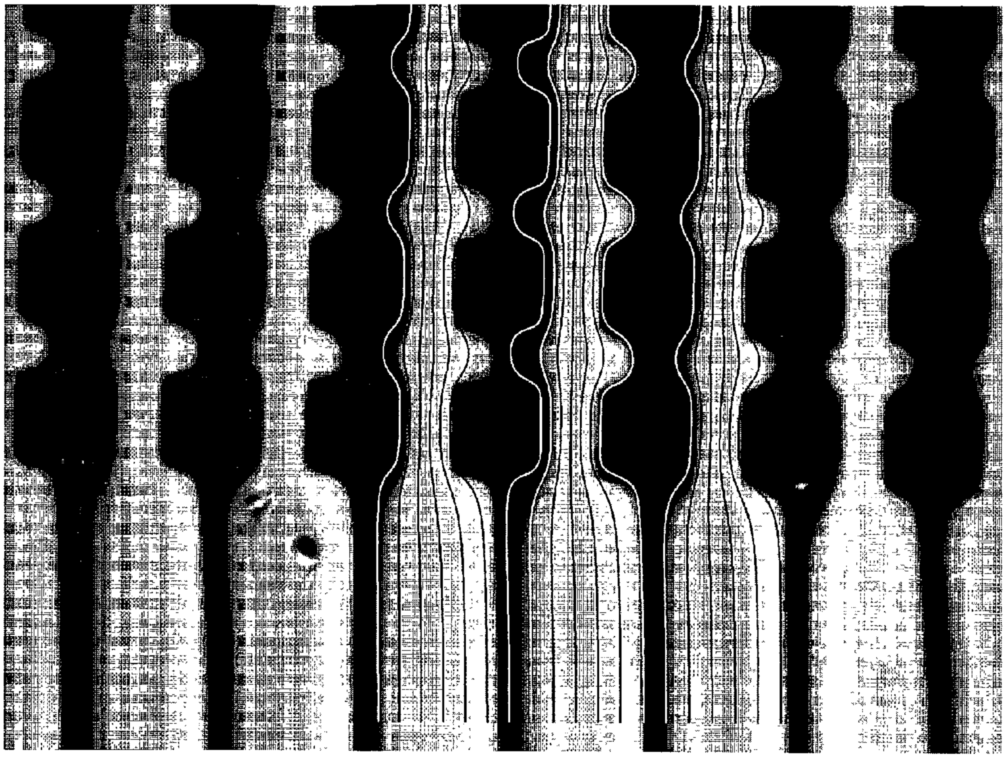
FIG. 12 shows the particle-concentration variation in particle flow past the end of a uniform square array of square posts having sides 36 μm long and arranged on 63-μm centers.

FIG. 12 shows the particle-concentration variation in particle flow past the end of a uniform square array of square posts having sides 36 μm long and arranged on 63-μm centers. The properties of the array are otherwise the same as those of the previous array. However, in contrast to the example shown in FIG. 11, the approximately 80 V/mm mean field is applied at an angle of 1.6° with respect to the principal axis of the array of posts. This angle of attack produces filaments that are slightly asymmetrical with respect to the columns of square posts. Again, the filaments align with the calculated electrokinetic flow streamlines. In this case, the large stagnant regions of the flow between the posts are highly depleted of particles. There is no evidence of filaments having significantly enhanced concentration as seen in FIG. 11. In fact, the difference between these images is a striking demonstration of the importance of post shape in the dielectrophoretic behavior of an array.

Figure 13:
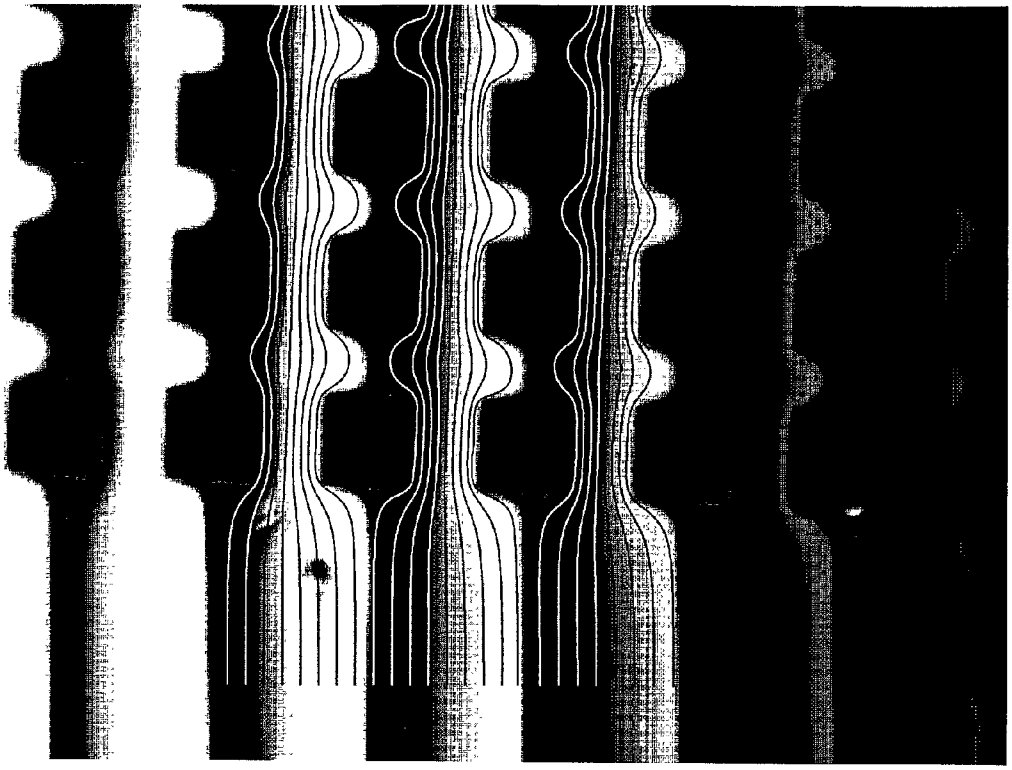
FIG. 13 shows the particle-concentration fields at the base of the same array as in FIG. 12 but with the electric field applied at an angle of approximately 3° with respect to the principal axis of the array of posts.

FIG. 13 shows the particle-concentration fields at the base of the same array as in FIG. 12 but with the electric field applied at an angle of approximately 3° with respect to the principal axis of the array of posts. The asymmetrical concentration gradient is seen to be dramatically steep toward the left of the post columns and relatively diffuse toward the right. The columns of posts produce a dielectrophoretic potential barrier that the fluid, but not the particles, can cross, the basis for depletion-mode DEP devices as described earlier.

Figure 14:
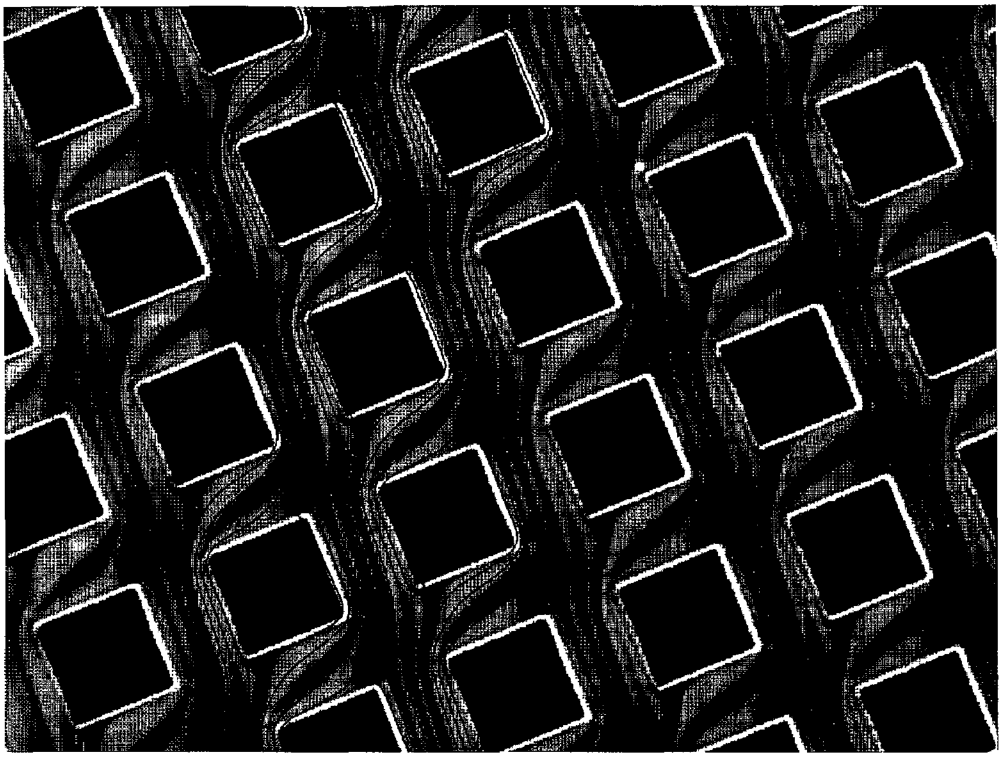
FIG. 14 shows the particle-concentration field in the center of an array of posts with the same properties as those of FIGS. 12 and 13 but with the principal axis of the array oriented at 20.5° with respect to the applied electric field of approximately 80 V/mm.

FIG. 14 shows the particle-concentration field in the center of an array of posts with the same properties as those of FIGS. 12 and 13 but with the principal axis of the array oriented at 20.5° with respect to the applied electric field of approximately 80 V/mm. In this flow, the variation in concentration is much weaker than in the previous examples because of the limited cooperative effect of the posts. The concentration gradients are only weakly coherently enhanced by the array since the streamline patterns approximately repeat after an offset of 5 rows and 2 columns rather than the offset of approximately 1 row in the previous figures. This example shows how it is important in designing these devices to limit the tilt angle of the array or to modify the post shape to support the large tilt angles as described earlier.

Figure 15:
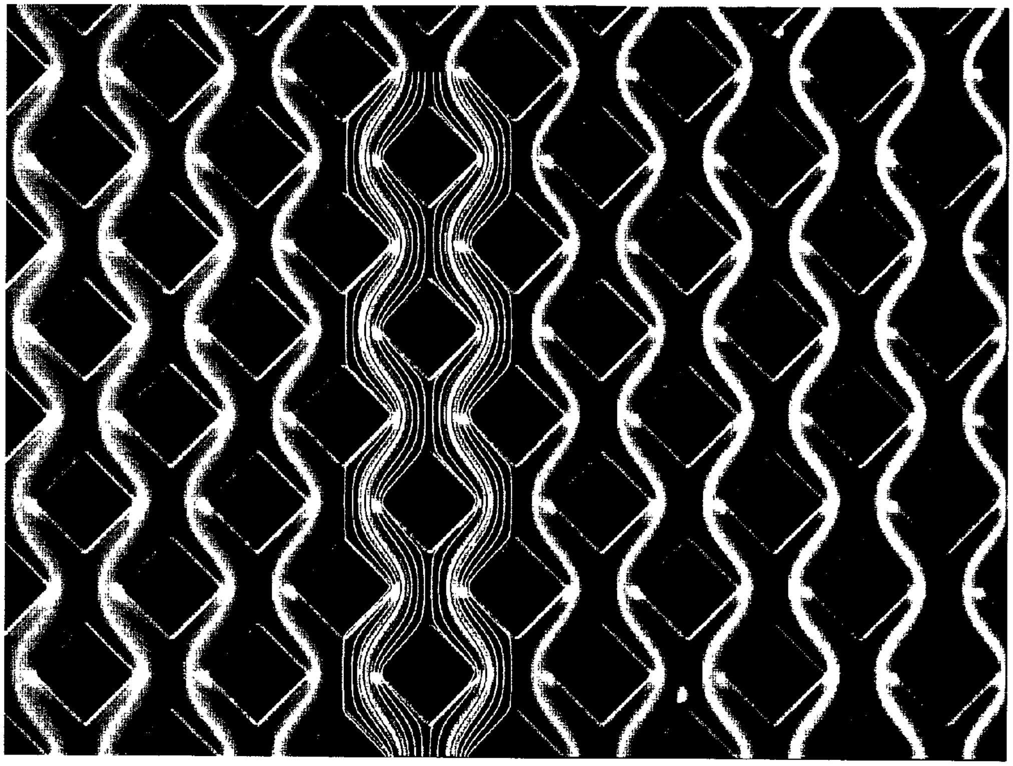
FIG. 15 shows the particle-concentration field in the center of a square array similar to those in the previous figures but with an electric field of 80 V/mm applied at angle of approximately 45.3° with respect to the principal axis of the array (approximately 0.3° with respect to a secondary axis).

FIG. 15 shows the particle-concentration field in the center of a square array similar to those in the previous figures but with an electric field of 80 V/mm applied at angle of approximately 45.3° with respect to the principal axis of the array (approximately 0.3° with respect to a secondary axis). In this example, the streamline pattern approximately repeats after an offset of 1 row and 1 column. The diagonal orientation of the square posts creates a large electric field concentration at the left and right vertices. The dielectrophoretic effect adds coherently in the array to produce a filament of high particle concentration that travels down the streamline at center of the channels. This is an example of an "enhancement-mode" device. This effect significantly reduces the interactions of the particles with the posts.

FIG. 16 is a graphical representation of the combined electrokinetic and DEP potential within unit cells comprising three kinds of uniform arrays. The flow in these arrays is from top to bottom. Isopotentials are lines of constant phase along a fringe. Adjacent fringes correspond to one tenth of the cell unit-potential difference. The potential difference across the cell, the size of the cell and the electrokinetic mobility of the particles are normalized to unity. Because of the substantial absence of inertia, particles travel in paths normal to the isopotentials. The left-most images show the undisturbed electrokinetic potential within the arrays. The other images show the distortion of the combined electrokinetic and DEP potentials of particles having a relative DEP mobility of 0.0125, 0.025, and 0.05. Trapping zones (for positive DEP particles) appear in the lower-left and right sides of the circular posts. Smaller zones appear for the on-axis square array. The 45° square array shows the formation of strong and sizable trapping zones even at low DEP mobility. The depth of the potential well of the traps is proportional to the number of fringes that curve around the well.

FIG. 17 shows the flow in the interior of the array of FIG. 11, however, at an applied electric field of approximately 100 V/m. The bright regions to the lower left and right of the circular posts contain trapped particles. Relatively weak fluorescence from concentrated filaments is evident along the streamlines near the regions of trapped particles. This image was recorded after the trapped regions had apparently reached steady state, about 5 seconds after the electric-field forcing started. The zones where particles are trapped are consistent with the location of the wells in the combined potential fields in FIG. 16.

Under conditions where particle trapping occurs, i.e., where the electric field applied to a fluid flowing through an array of insulating posts or columns is equal to or greater than some minimum value, that can depend upon the shape of the insulating structures as well as the composition of the fluid and particles, the particles can be assumed to be effectively immobilized within traps formed around the insulating posts disposed in the flow channel (cf. FIG. 17). Dispersive separations can be performed by ramping the amplitudes of the alternating or quasi-steady components of the applied electric field and consequently the depth of the traps. This ramping can be monotonic, analogous to a gradient elution in chromatography, or repeated.

Arrays such as that shown in FIG. 17 can also be used as gated traps or particle concentrators by applying an electric field to collect particles having a dielectrophoretic mobility above the trapping threshold produced by that field. When the applied field is lowered or made zero, the particles can be released in a concentrated stream, possibly to a secondary flow channel. A similar device that concentrates particles, while spatially segregating them by their dielectrophoretic mobility can be made by tapering the channel to concentrate the electric field at one end or by changing the post dimensions or shape across the array or a combination of these two methods.

Both filamentary and trapping DEP phenomena can be utilized in a cyclic-transport system. In many applications of DEP, an alternating electric field is employed to generate a low-frequency or near steady DEP force. In contrast, the cyclic forcing here results from periodically changing the magnitude of this near-steady DEP force.

Figure 18:
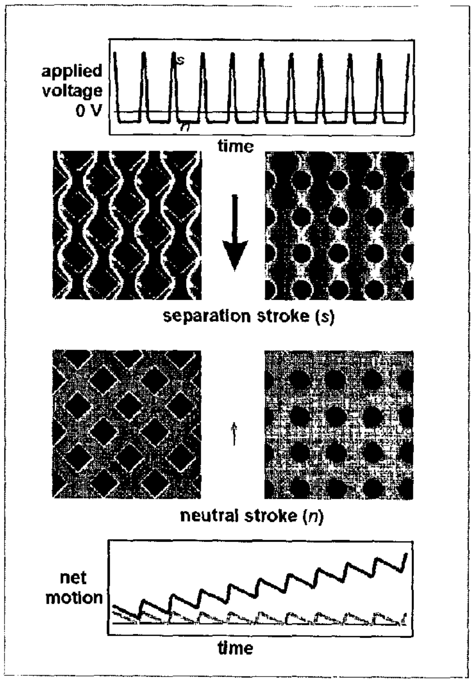
FIG. 18 shows examples of cyclic separations based upon filamentary DEP in circular- and square-post arrays.

FIG. 18 shows examples of cyclic separations based upon filamentary DEP in circular- and square-post arrays. Depending on the geometry of the posts, positive DEP particles can be advanced or retarded compared to dielectrophoretically neutral particles. In the first and second steps of the cycle, filaments form and propagate as shown in the top inset images. In the third and fourth steps, the filaments disappear and the particles flow without bias back up the array as shown in the lower inset image. A cycle having a non-zero average applied field can be used to superimpose any desired field-linear particle transport.

Figure 19:
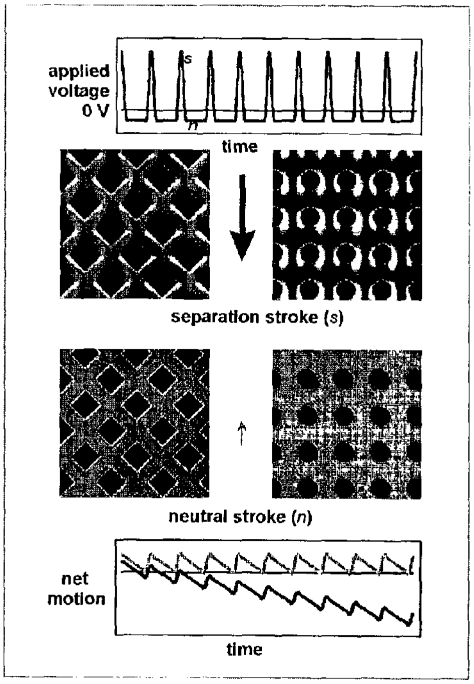
FIG. 19 illustrates cyclic separations based upon trapping DEP.

FIG. 19 illustrates cyclic separations based upon trapping DEP. In the first and second steps of the cycle, the particles enter traps and are immobilized or severely retarded while the unaffected fluid flows as shown in the upper inset image. In the third and fourth steps, the traps are released and both the particles and fluid flow freely back up the array as shown in the lower inset image.

The foregoing is intended to be illustrative of the present invention and is provided for purposes of clarity and understanding of the principles of this invention. Many other embodiments and modifications can be made by those of skill in the art without departing from the spirit and scope of the invention as defined in the following claims.

What is claimed is:

1. A method for spatial separation of particles, comprising:

providing a fluid flow channel having first and second ends, a fluid inlet port at the first end, a filtered output port and a concentrate output port at the second end in fluid communication with the flow channel, and electrodes in electric communication with the inlet and outlet ports, wherein the flow channel is disposed on a substrate, and wherein the flow channel has a plurality of insulating posts disposed therein between the inlet and output ports;

admitting a fluid containing a suspension of particles to the flow channel through the fluid inlet port;

applying an electric field to the suspension to effect continuous flow dielectrophoretic separation of the particles; and extracting the separated particles from the concentrate output port, wherein the plurality of insulating posts are arranged in an array having a primary principal axis, and wherein the primary principal axis of the array is tilted relative to the applied electric field.

2. The method of claim 1, wherein spatial separation comprises filtration, concentration, or fractionation.

3. The method of claim 1, wherein the array of insulating structures is shaped so as to concentrate the electric field.

4. The method of claim 1, wherein the substrate is a glass material.

5. The method of claim 1, wherein the substrate is a polymer material.

6. The method of claim 1, wherein the insulating posts are about 1 μm to about 100 μm across.

7. The method of claim 1, wherein the primary principal axis of the array is tilted relative to the applied electric field by about 0.5° to about 15°.

8. An apparatus for spatial separation of particles, comprising:

a fluid flow channel having first and second ends disposed on a substrate, wherein said fluid flow channel is provided with a fluid input port at the first end, a filtered output port and a concentrate output port at the second end in fluid communication with the fluid flow channel, and wherein the flow channel has a plurality of insulating structures disposed between the input and output ports;

electrodes in electric communication with the fluid inlet and output ports; and power supply means connected to said electrodes to generate an electric field within said flow channel, wherein the plurality of insulating structures are arranged in an array having a primary principal axis, and wherein the primary principal axis of the array is tilted relative to the applied electric field, wherein the apparatus is a continuous flow apparatus, and wherein the primary principal axis of the array is tilted relative to the applied electric field by about 0.5° to about 15°.

* * * * *